United States Patent [19]

Smits

[11] Patent Number: 5,711,307
[45] Date of Patent: Jan. 27, 1998

[54] METHOD AND APPARATUS FOR DETECTING MYOELECTRIC ACTIVITY FROM THE SURFACE OF THE SKIN

[75] Inventor: Matthijs P. Smits, Ashland, Mass.

[73] Assignee: Liberty Mutual Insurance Company, Boston, Mass.

[21] Appl. No.: 421,602

[22] Filed: Apr. 13, 1995

[51] Int. Cl.$^6$ ............................................. A61B 5/04
[52] U.S. Cl. .................................................. 128/733
[58] Field of Search ................................ 128/733, 774, 128/782, 905; 327/1

[56] References Cited

U.S. PATENT DOCUMENTS

| | | | |
|---|---|---|---|
| 4,170,225 | 10/1979 | Criglar et al. | 128/733 |
| 5,085,225 | 2/1992 | DeLuca et al. | 128/733 |
| 5,085,226 | 2/1992 | DeLuca et al. | 128/733 |
| 5,086,779 | 2/1992 | DeLuca et al. | 128/733 |
| 5,233,999 | 8/1993 | Dellacoma et al. | 128/733 |
| 5,318,039 | 6/1994 | Kadefors et al. | 128/733 |
| 5,341,813 | 8/1994 | Teare et al. | 128/733 |

OTHER PUBLICATIONS

RED Annual Report 1991, "A Portable Muscle–Site Identification System", pp. 95–96.

Hanson et al., "The Liberty Myoarray ™: A Diagnostic Tool to Test and Train Amputees to Use Myoelectric Prostheses", Proceed. Int'l Symp. on Myoelectric Control, Future Trends in Myoelectric Technology, U of New Brunswick, Fredericton, NB, Canada, Aug. 16, 1993.

Meek et al., "Comparison of signal–to–noise ratio of myoelectric filters for prosthesis control", Jrnl. of Rehab. and Dev., vol. 29, No. 4, pp. 9–20, 1992.

Thusnevapan et al., "A Practical Electrode–Array Myoprocessor for Surface Electromyography", IEEE Transactions on Biomedical Engineering, vol. 36, No. 2, pp. 295–299, Feb. 1989.

*Primary Examiner*—Max Hindenburg
*Attorney, Agent, or Firm*—Wolf, Greenfield & Sacks, P.C.

[57] ABSTRACT

An apparatus for detecting myoelectric activity from the surface of the skin has an electrode pair, processing circuitry, and up to three output leads. The signals detected at the electrode contacts are differentiated, amplified, and then filtered. The filtered signals are provided as a first input signal to a switch and a ground signal is provided as a second input signal to the switch. The amplified, unfiltered signals are tested against a preset threshold. If the signals exceed the threshold, the signals are considered to have significant amounts of noise. In this case, a comparator causes the switch to provide the ground signal as the output signal. Otherwise, the switch provides the filtered signals as the output signal. One output line provides the amplified, unfiltered signals for testing and analysis. The apparatus can be used as part of a prosthetic device, or can be used for testing with a plurality of electrode pairs.

11 Claims, 2 Drawing Sheets

METHOD AND APPARATUS FOR DETECTING MYOELECTRIC ACTIVITY FROM THE SURFACE OF THE SKIN

FIELD OF THE INVENTION

The invention relates to the detection and analysis of myoelectric signals detected from the skin.

BACKGROUND OF THE INVENTION

Myoelectric signals that are detected at the surface of the skin are a summation of muscle motor unit firings. Because these firings are inconsistent, the myoelectric signals contain frequency components that vary in amplitude throughout the frequency spectrum. As detected, these signals are a function of anatomical and physiological factors, as well as various filtering features of the environment and of the electrodes and circuitry used for detection. The myoelectric signals traverse muscle, fatty tissues, and skin tissues, all of which act as a low pass filter, since higher frequency components are progressively more attenuated as the tissue depth increases. Upon reaching the electrodes at the surface of the skin, the characteristics of the electrodes and electrolytes of the skin serve as a high pass filter. When the signals reach the detection apparatus, further bandpass filtering is provided by the configuration of the electrode, amplifiers, and other circuit elements. The resulting detected surface myoelectric signal has a frequency spectrum that ranges from about 20–400 Hz, and has a maximum amplitude that ranges from about 0.5–2 mV.

When receiving myoelectric signals, it is preferable that they contain as little noise as possible. The noise that is encountered in detecting the myoelectric signals can be separated roughly into four categories: (1) extrinsic electrical noise, including all the sources that have nothing to do with the actual detection of myoelectric signals, such as lighting, heating, power lines, switching power supplies, and electrical equipment (2) biomechanical noise, including movement artifacts, which occur when the electrode and the skin move relative to one another (3) bioelectrical noise, which includes electrical activity from within the human body and not related to muscle activation, such as neural evoked potentials and (4) intrinsic electrical noise, which includes all the sources of noise from the detection apparatus, e.g., noise from operational amplifiers.

Generally, for detecting a myoelectric signal, a differential amplifier is used with an electrode pair. The electrode pair senses the voltage potential at two locations, while a reference electrode is provided at an electrically neutral location. The differential amplifier rejects almost all of the common modes by applying positive and negative amplification to the two received signals and adding them algebraically.

Biomechanical noise, which includes movement artifacts, typically provides large, low frequency signals that do not necessarily occur at both electrode contacts at the same time. Therefore, an electrode pair configuration with differential amplifier does not necessarily eliminate these sources of noise.

Both extrinsic electrical noise and biomechanical noise can occur when only one of the electrode contacts is in contact with the skin, since the electrode that is not on the skin acts as an antenna. In this situation, extrinsic electrical noise is far greater at the electrode contact which is not connected to the skin. Differentiating the signals from the electrodes leaves significant noise that contaminates the detected myoelectric signals. These two types of noise sources are frequently detected in dynamic situations where myoelectric activity is monitored as part of research studies or as a control input to prosthetic devices.

SUMMARY OF THE INVENTION

The invention features a method and apparatus for detecting myoelectric activity from the surface of the skin. The apparatus has an electrode arrangement, preferably an electrode pair, for picking up myoelectric signals from the surface of the skin, and circuitry for processing the detected signal. A first signal derived from the myoelectric signal is compared to a threshold in a comparator. The comparator controls whether a second signal derived from the myoelectric signal or a reference signal will be provided as an output. The reference signal is preferably a ground signal, while the threshold is preferably selected to be about a maximum expected level for the first signal. If the first signal exceeds this threshold, the comparator causes the ground signal to be output. It is assumed that if the first signal exceeds the maximum, it has too much noise.

In preferred embodiments, the electrode pair is placed on a selected muscle and the patient performs a muscle contraction. The voltage signals detected at the two electrodes are differentiated and amplified. The resulting differentiated, amplified voltage signals are provided to at least two branches, or preferably three branches if the circuit is used for analysis. On a first branch, the signals are buffered and provided to a user. These "raw" signals can be useful for analysis.

On a second branch, the differentiated, amplified signals are bandpass filtered and buffered, and the resulting filtered signals are provided as a first input signal to a switch. A second input to the switch is a reference voltage, preferably ground. For the switch, a control signal input, which determines whether the first or second input to the switch is output, is provided by a third branch. The output signal from the switch is provided to a gain and buffer stage. The buffered signal is then provided to an output lead.

On the third branch, the differentiated, amplified signals are further amplified, full-wave rectified, smoothed, and provided to a comparator so that the second signal derived from the myoelectric signal is preferably a DC voltage signal with minimal ripple. The comparator compares the DC voltage signal to a reference voltage, and provides an output signal that is coupled to the switch as the control signal. When the DC voltage signal is lower than the reference threshold, the comparator causes the switch to provide the filtered signals as an output. When the input signals are higher than the reference threshold, the comparator causes the switch to switch the output to ground.

The reference voltage provided to the comparator is set to be about the maximum voltage that is expected to be received by the comparator, given the maximum voltage level that is provided by the electrodes and given the combined amplification caused by circuit components. Voltage levels exceeding the reference voltage are assumed to be excessive due to noise. The output of the comparator can also be provided at an output lead for analysis. The status of the comparator indicates, in an essentially binary manner, when the signals exceed that threshold, and hence when noise causes the output to be excessively large.

A circuit according to the present invention can be used for detecting signals for analysis, or can be provided to a motor in a prosthetic device, preferably through a rectifier and a smoothing stage. In addition, multiple circuits can be provided for use with an array of electrode pairs, or a single circuit can be provided with appropriate selection circuitry.

For an array, such a circuit can be particularly useful since there is more risk that an electrode may become separated from the skin.

BRIEF DESCRIPTION OF THE DRAWINGS

Other features and advantages will become apparent from the following detailed description and from the drawings in which.

DETAILED DESCRIPTION

Figure 1:
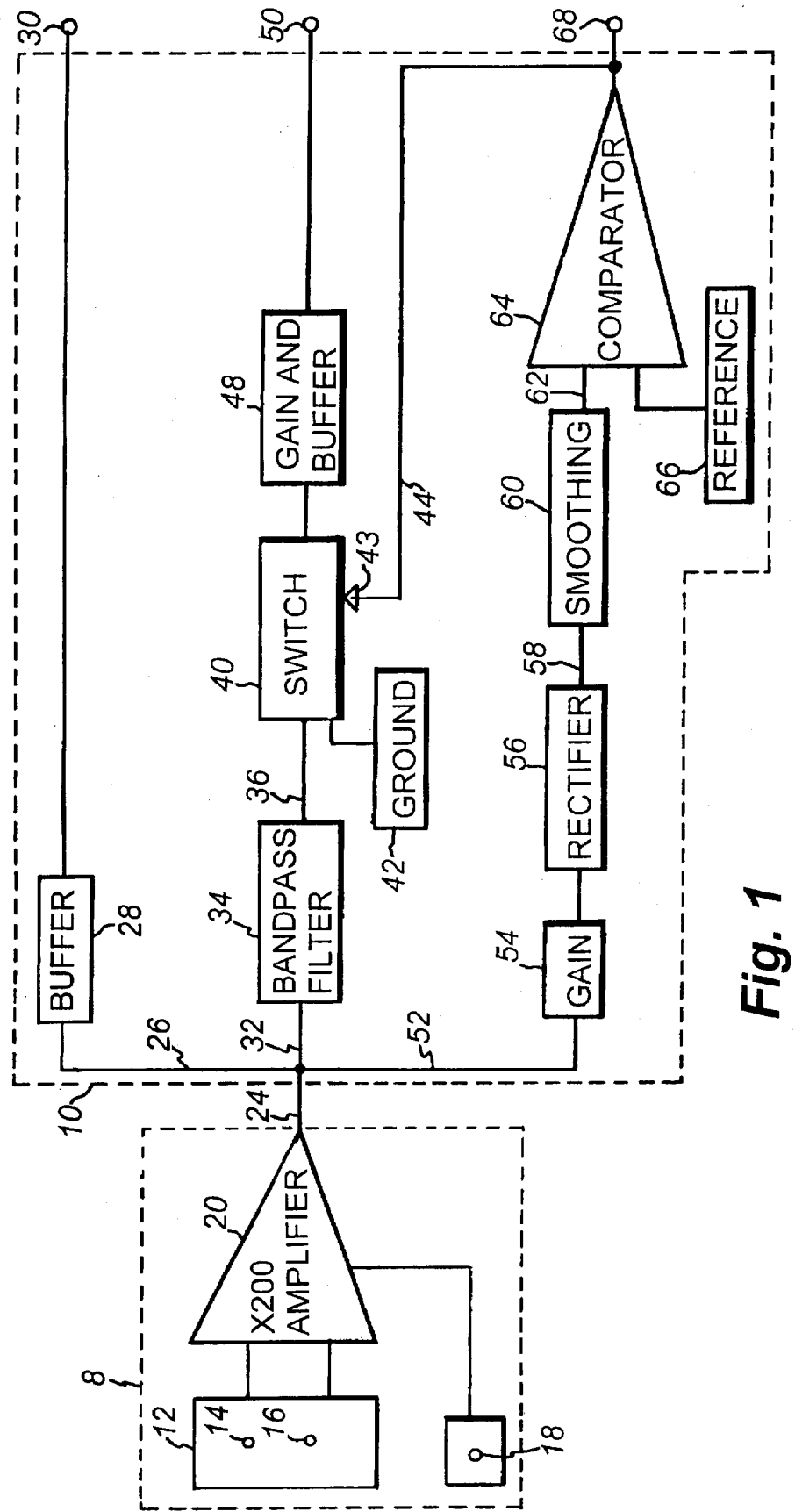
FIG. 1 is a schematic block diagram of a circuit according to the present invention.

Referring to FIG. 1, a circuit 10 can be used in a system for detecting, testing, and analyzing myoelectric signals, and can also be used for operating a prosthetic limb, such as a Boston Elbow, a prosthetic arm available from Liberty Mutual Insurance Co. of Boston, Mass..

An electrode circuit 8 includes an electrode pair 12 having two individual spaced electrodes 14, 16 positioned on the skin of a patient (not shown) for detecting myoelectric signals from a muscle, such as a bicep or a tricep. A ground electrode 18 is positioned at a location where there is little muscle activity, such as an armpit. The myoelectric signals that are received from the electrode pair, which have a maximum voltage of about 0.5 to 2.0 mV, are provided to a differential amplifier 20, which provides an amplified voltage signal 24. Amplifier 20 has a gain of about 10–1000, but more typically about 200. Differential amplifier 20 removes most of the common modes of noise as noted above.

Amplified voltage signal 24 is provided to three branches. Since signal 24 can be useful for testing and analysis, if circuit 10 is used for analysis, signal 24 is provided along a first branch 26 to a buffer 28, which then provides signal 24 as an output signal at a first output lead 30. Along a second branch 32, signal 24 is provided to a bandpass filter 34 which outputs a filtered signal 36 in a frequency range of about 30–400 Hz. Filtered, amplified signal 36 is provided as a first input to a switch 40. A second input to the switch is coupled to a fixed reference voltage source, such as a ground signal 42. Switch 40 has a control lead 43 for receiving a control signal 44 that controls whether switch 40 provides filtered amplified signal 36 or ground signal 42 as an output. The output of switch 40 is provided to a gain and buffer stage 48, which provides an output signal at lead 50.

Switch 40 is controlled by a third branch 52. Amplified signal 24 is again amplified about 1–10 times in a gain stage 54. The resulting amplified voltage signal is provided to a full wave rectifier 56 to convert the signal to a positive voltage signal 58. The rectified signal is smoothed with a smoothing stage 60 that preferably includes an RC circuit with high capacitance to reduce any ripple signal. The smoothing stage does, however, reduce some of the gain. The smoothed signal 62 is thus a DC voltage signal that is derived from the signal from electrode circuit 8 and that is provided as a first input to a comparator 64. The comparator receives a reference voltage 66 as a second input.

An output signal from the comparator 64 is coupled to the control input 43 of switch 40 as the control signal 44, and is based on the comparison between signal 62 and reference voltage 66. The reference voltage is selected to be about a maximum expected voltage of signal 62. Accordingly, if signal 62 provided as the first input to the comparator exceeds the reference voltage, it is assumed that signal 62, and therefore also signal 36, has too much noise. Accordingly, the comparator causes switch 40 to output ground signal 42. If the smoothed signal is less than the reference voltage, switch 40 provides filtered, amplified signal 36 to gain and buffer stage 48.

Control signal 44 output from comparator 64 can also be provided at an output lead 68. Control signal 44 is essentially a binary signal that is useful for determining when and how often signal 62 exceeds reference voltage 66. From this data, a user can determine if there is an occasional excess of noise, or a systemic problem in detecting myoelectric signals.

The gain in differential amplifier 20, the gain in the gain stages 48 and 54, and reference voltage 66 can all be fixed or adjustable. If the reference voltage is fixed at a value $V_R$, and the maximum output voltage from the electrode pair is determined to be $V_{max}$ (e.g., 2 mv), the combined gain should ideally be about $V_R/V_{max}$, i.e. $V_R=(V_{max})*(gain)$. The combined gain will actually be less than the product of the amplifier stages, however, because of some attenuation from the smoothing stage. This attenuation can be determined empirically or estimated.

The circuit according to the present invention thus provides up to three output signals: a raw differentiated, amplified signal; the differentiated, amplified signal further filtered and amplified in some instances, and a ground signal in other instances and an output signal indicating whether certain types of noise, particularly extrinsic or biomechanical noise, are excessive.

Figure 2:
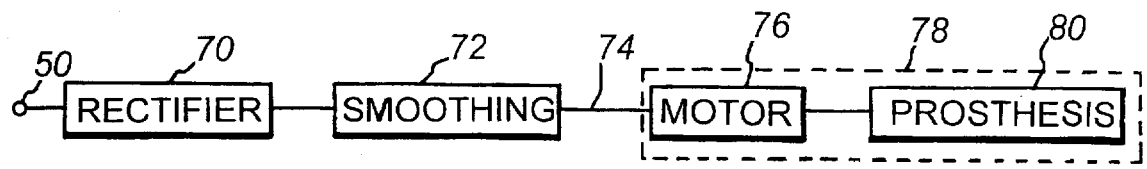
FIG. 2 is a schematic block diagram of a circuit for coupling to an output of the circuit of FIG. 1.

Referring to FIG. 2, if the circuit is used for controlling a prosthetic device, the amplified buffered signal provided at output lead 50 is provided to a full-wave rectifier 70 and a smoothing circuit 72. The resulting voltage signal is coupled to a motor 76, which is part of the prosthetic device 78, for driving prosthesis 80. In this case, first branch 26 can be omitted, and control signal 44 need not be provided at output lead 68.

Figure 3:
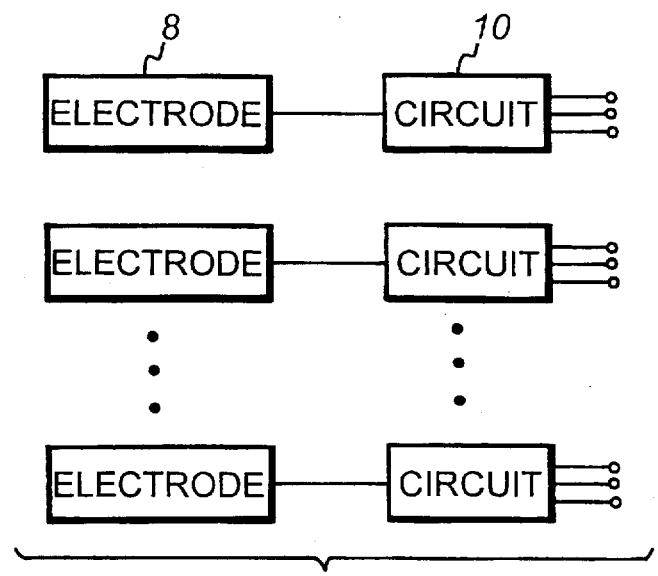
FIGS. 3 and 4 are schematic block diagrams of two different embodiments of the circuits of FIG. 1 used with an array of electrodes.
Figure 4:
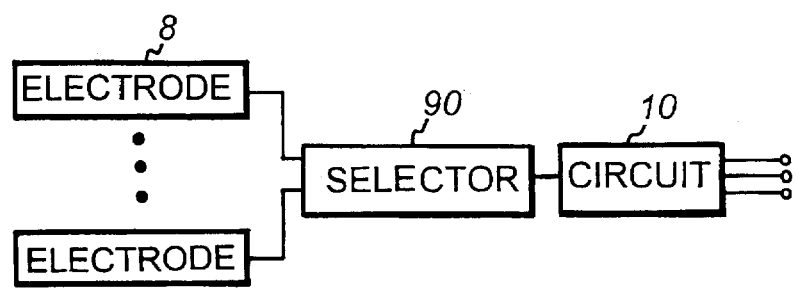

Referring to FIGS. 3 and 4, a circuit according to the present invention can be coupled to an array of electrode pairs for testing. Since there may be numerous electrode pairs in an array, circuit 10 may be particularly useful because it is more likely that one electrode in a pair will be out of contact. The array, may be like the one shown, for example in U.S. Pat. No. 5,341,813, which is assigned to the assignee of the present invention and which is expressly incorporated herein by reference. The array in that patent has electrodes preferably arranged in a two-dimensional array with N×M electrodes forming N×(M−1) electrode pairs, where the electrodes on the columns are fixed relative to each other in a longitudinal direction and where the columns have some elasticity in the transverse direction.

Referring to FIG. 3, a circuit 10 can be provided for each respective electrode pair in an array; or, referring to FIG. 4, a selection circuit 90 can be provided intermediate the pairs and a single circuit.

While the switch is shown here in a representative form, it would typically have one or more electrical components.

Having described a preferred embodiment of the present invention, it should become apparent that other changes and modifications can be made without departing from scope of the appended claims. The comparator and switch, for example, can be arranged in a number of different ways.

What is claimed is:

1. An apparatus for use with a myoelectrode that provides a myoelectric signal, the apparatus comprising:

a comparator, electrically coupled to the myoelectrode, for receiving a first signal derived from the myoelectric signal and for comparing the first signal to a threshold signal, the comparator providing an output signal indicating whether or not the first signal exceeds the threshold signal; and a switch, electrically coupled to the myoelectrode and to the comparator, for receiving a second signal derived from the myoelectric signal and for receiving a control signal derived from the output signal of the comparator, the switch providing at an output lead an output signal in response to the control signal.

2. The apparatus of claim 1, wherein the switch also receives a ground signal, wherein the switch provides at the output lead the ground signal when the control signal from the comparator indicates that the first signal exceeds the threshold signal.

3. The apparatus of claim 2, wherein the threshold signal is selected to be based on a maximum expected voltage of the first signal.

4. The apparatus of claim 1, wherein the threshold signal is selected to be based on a maximum expected voltage of the first signal.

5. The apparatus of claim 4, wherein the signal at the output lead is provided to a motor that drives a prosthetic device.

6. The apparatus of claim 1, wherein the apparatus includes means for coupling the comparator and switch to at least one of a plurality of myoelectrodes.

7. A circuit for use with a myoelectrode that detects a myoelectric signal from a surface of a patient's skin, the circuit comprising:

a comparator including:
      a first input lead receiving a first signal derived from the myoelectric signal,
      a second input lead receiving a threshold signal,
      circuitry comparing the first signal and the threshold signal, and
      an output lead that provides an output signal that indicates whether the first signal exceeds the threshold signal; and a switch including:
      a first input lead receiving a second signal derived from the myoelectric signal,
      a second input lead coupled to a reference signal,
      a control lead that receives a control signal derived from the output signal, and
      an output lead providing as an output one of the second signal and the reference signal in response to the control signal.

8. The circuit of claim 7, wherein the threshold signal is selected to be about equal to a maximum expected first signal, wherein the comparator provides an output signal that causes the switch to output the reference signal when the first signal exceeds the maximum expected first signal, and wherein the comparator causes the switch to output the second signal when the first signal does not exceed the maximum expected first signal.

9. The circuit of claim 8, wherein the second signal is a DC voltage signal.

10. A method for processing a myoelectric signal including the steps of:

determining whether a first signal derived from the myoelectric signal exceeds the reference signal;

providing, at a first output lead, a second signal derived from the myoelectric signal in response to a determination that the first signal does not exceed the reference signal; and providing, at the first output lead, a fixed reference voltage in response to a determination that the first signal exceeds the reference signal.

11. The method of claim 10, further comprising a step of providing at a second output lead a signal indicating how often the first signal exceeds the reference signal.

* * * * *